United States Patent [19]
Black

[11] 3,972,123
[45] Aug. 3, 1976

[54] AIR-ABRASIVE PROPHYLAXIS EQUIPMENT

[76] Inventor: Robert B. Black, 2925 Denver, Corpus Christi, Tex. 78404

[22] Filed: Dec. 11, 1974

[21] Appl. No.: 531,466

Related U.S. Application Data

[62] Division of Ser. No. 403,436, Oct. 4, 1973, Pat. No. 3,882,638.

[52] U.S. Cl. .................................................. 32/58
[51] Int. Cl.² .......................................... A61C 3/06
[58] Field of Search .................. 32/58, 59; 51/8, 11, 51/12

[56] References Cited
UNITED STATES PATENTS

| | | |
|---|---|---|
| 2,290,979 | 7/1942 | Luce ........................................ 51/11 |
| 2,376,287 | 5/1945 | Sorrentino ............................. 51/11 |
| 2,825,135 | 3/1958 | Tilden ..................................... 32/58 |
| 3,525,154 | 8/1970 | Lieb ........................................ 32/28 |
| 3,775,849 | 12/1973 | Condon ................................. 32/59 |

*Primary Examiner*—Robert Peshock
*Attorney, Agent, or Firm*—Synnestvedt & Lechner

[57] ABSTRACT

Air-abrasive equipment is provided for prophylaxis or tooth cleaning purposes. Provision is made for directing not only the air-abrasive stream or jet but also for directing a stream of warmed water, preferably in the form of a curtain surrounding the air-abrasive stream and serving to enhance the cleaning action and also to entrain the abrasive particles so that they may readily be withdrawn or removed through a liquid suction system.

5 Claims, 4 Drawing Figures

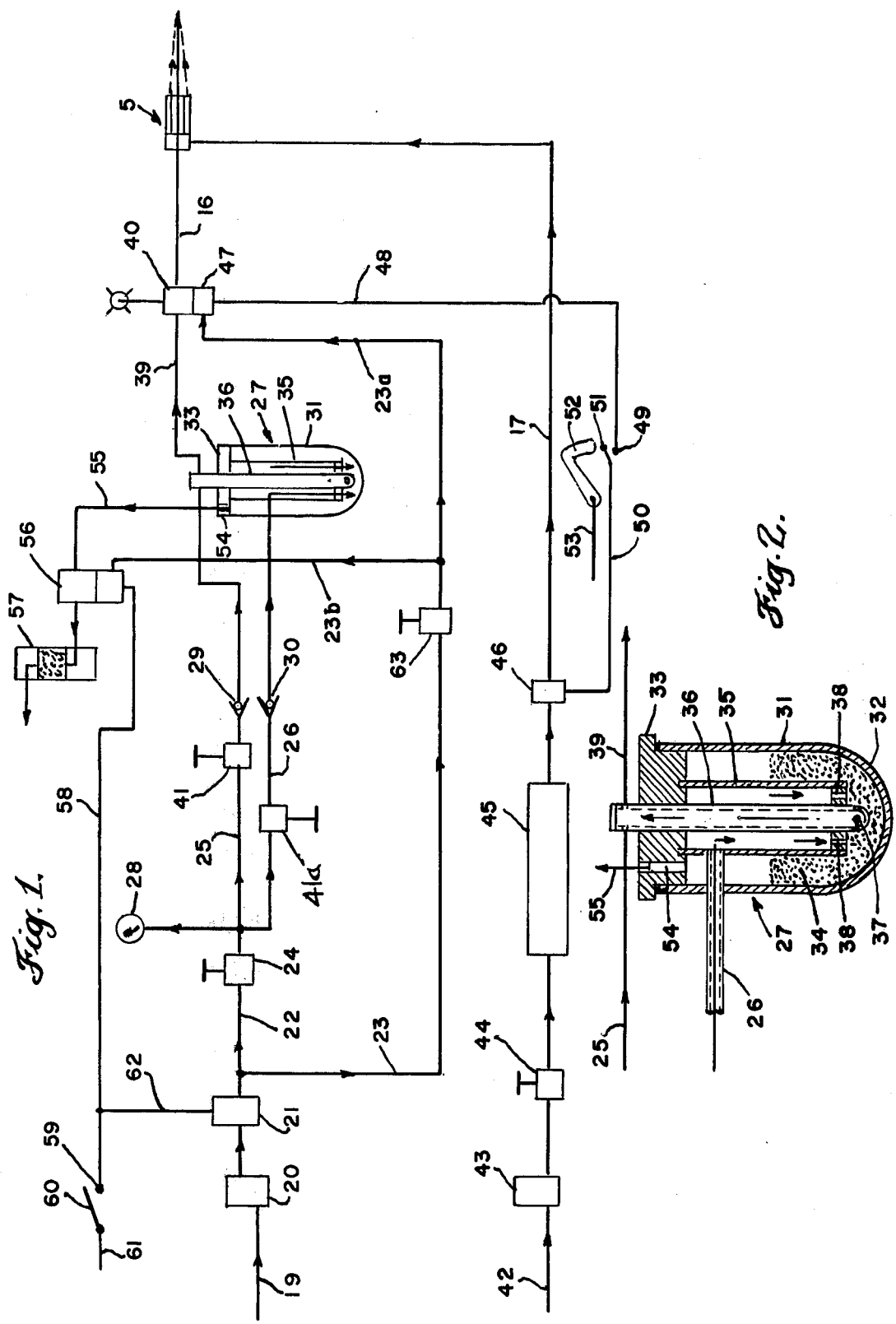

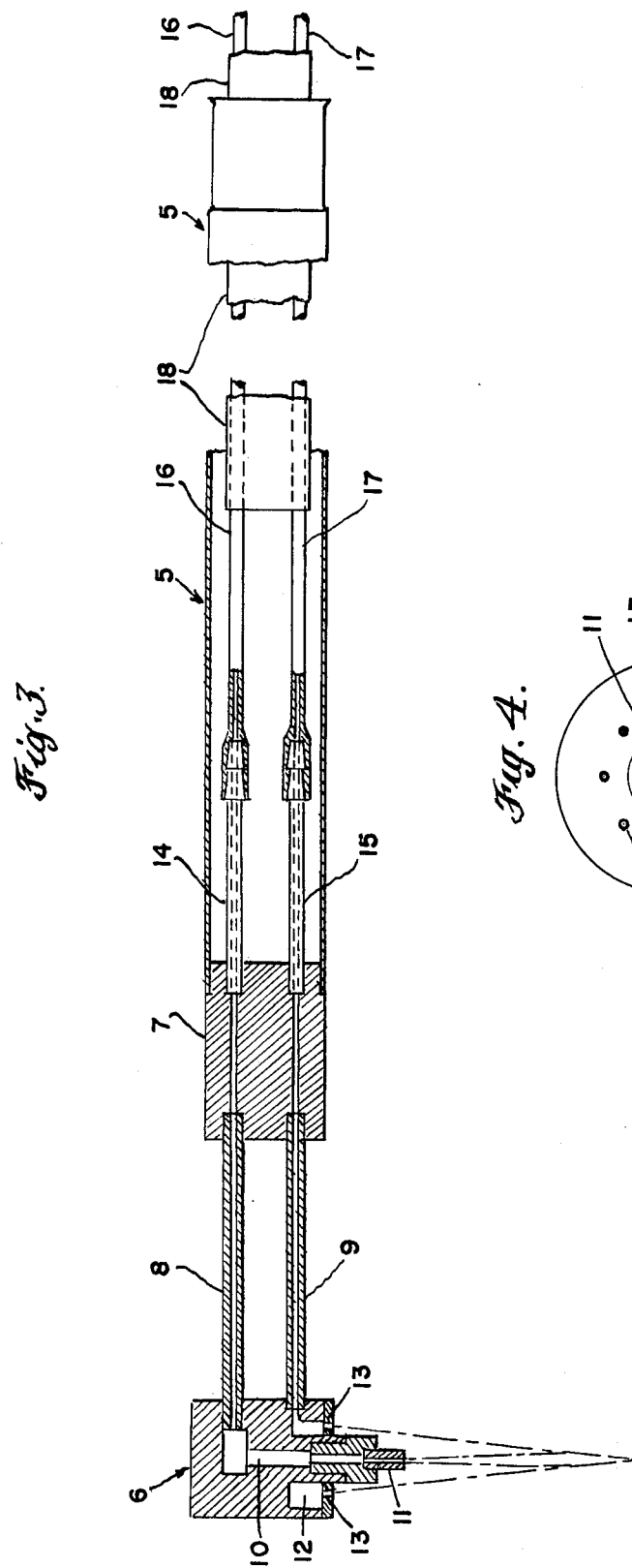

AIR-ABRASIVE PROPHYLAXIS EQUIPMENT

This is a division of application Ser. No. 403,436, filed Oct. 4, 1973 and issued May 13, 1975 as U.S. Pat. No. 3,882,638.

This invention relates to air-abrasive equipment and is particularly concerned with equipment of this type especially adapted for use in the cleaning of teeth, especially the removal of foreign material from the exposed surfaces of the teeth, such as those materials which are broadly classified as stain and calculus.

As is known, stain may originate from various sources or causes including smoking, tobacco chewing, excessive drinking of tea or from vegetable origin. Calculus is of several different types, especially serumal and salivary, and calculus deposits ordinarily accumulate in pockets between the teeth and the surrounding soft tissues, the serumal calculus originating from blood in this area and the salivary calculus originating from the saliva. These constituents precipitate and bond themselves to the exposed tooth surfaces.

Various techniques and equipment are already known and used in the cleaning of teeth, including hand instruments, rotary rubber cups carrying an abrasive paste of pumice or silex, all of which techniques may be used effectively in the removal of calculus, but none of which techniques are satisfactory in effecting the removal of various types of stain, especially the removal of stain from broad areas of the teeth.

The equipment and the technique of the present invention are not only usable in the removal of calculus, but are also particularly advantageous in the removal of stain which frequently occurs in relatively broad areas mixed with a thin coating of salivary calculus.

Air-abrasive equipment has been known and extensively used in dental work, but in general such air-abrasive equipment has been employed primarily in the cutting of the tooth structure in preparation for the filling of cavities. In contrast, the equipment of the present invention is especially adapted to the cleaning of teeth, particularly to the removal of stain, whether or not mixed with a coating of calculus.

In air-abrasive equipment used for dental purposes, the delivery and dispersal of abrasive particles in air suspension in the mouth is objectionable and in some prior equipment employed for tooth cutting, vacuum means such as an exhaust blower has been employed. This, however, is bulky and cumbersome. In some prior systems it has also been contemplated to wash the teeth with water following the abrasive treatment, but such subsequent washing does not overcome the objectionable initial distribution of the abrasive particles on the soft tissues and other parts of the mouth.

It is an object of the present invention to overcome the various difficulties and disadvantages above referred to and to provide an airbrasive prophylaxis equipment adapted to the convenient and effective removal of stain and or calculus in a manner which is simple and which produces minimum discomfort to the patient.

According to the invention the equipment includes a hand piece having a nozzle with an air-abrasive discharge passage and further having a series of water discharge passages in an array surrounding the air-abrasive passage, together with control means by which warmed water is delivered for discharge through the array of water passages and by means of which the control of the air-abrasive and water streams is coordinated in a manner assuring the delivery of water at all times when the air-abrasive stream is being delivered.

In the hand piece provided according to the present invention the water discharge passages are arranged to impinge upon the surface of the tooth being cleaned in an area immediately adjacent to the area of impingement of the air-abrasive stream. Preferably a plurality of water streams are provided arranged in the manner of a curtain surrounding the air-abrasive stream. By positioning the water streams to impinge upon the tooth surface adjacent to but not coincident with the target area of impingement of the air-abrasive stream, the full effectiveness of the air-abrasive stream for its intended prophylaxis purpose is assured, while, at the same time, the water is present in the immediate vicinity of the target area of the abrasive stream, so that the abrasive particles are immediately taken up in suspension in the water and will flow with the water away from the tooth surface being cleaned for removal from the mouth as by the commonly used suction tube.

How the foregoing and other objects and advantages are attained will appear more fully from the following description referring to the accompanying drawings in which:

FIG. 1 is a schematic diagram of equipment according to the present invention including a hand piece having an air-abrasive discharge passage and also water discharge passages, together with supply and control mechanism for the abrasive and water;

FIG. 2 is an enlarged sectional view of a device for mixing abrasive particles with an air stream to be delivered to the hand piece;

FIG. 3 is a view of the hand piece, with the parts in section so as to illustrate the interior construction, especially of the head of the hand piece; and FIG. 4 is a detailed view showing the arrangement of the air-abrasive nozzle and of the surrounding array of water discharge passages.

Referring first to FIGS. 3 and 4, the hand piece comprises a tube 5 by which the instrument is to be held when in use in the mouth. The head of the hand piece is generally indicated by the reference numeral 6, and it will be seen that the head is supported at one end of the tube 5 by means of the block 7 and the connected tubes 8 and 9. Tube 8 connects with the central passage 10 in the head which in turn connects with the abrasive nozzle 11 having a discharge passage extended at right angles to the axis of the handle 5.

Tube 9 connects with the annular chamber 12 surrounding the passage 10 and the air-abrasive nozzle, the chamber 12 serving as a supply chamber for the series of water discharge passages 13.

As will be seen from FIGS. 3 and 4 the water discharge passages 13 are arranged in an array surrounding the air-abrasive nozzle 11 and the water passages are preferably inclined somewhat toward the air-abrasive stream, but this inclination is relatively slight and should not be so great as to intersect or join the air-abrasive stream at a point in advance of the impingement of the air-abrasive stream against the tooth surface being cleaned.

It will be seen that the air-abrasive and water nozzle arrangement provides a curtain or envelope of water surrounding but spaced from the air-abrasive stream in the target area of the air-abrasive stream, so that the action of the abrasive particles is not impaired at the target area. At the same time the envelope or curtain of water will merge with the air-abrasive stream at least beyond the normal air-abrasive target distance from the head of the hand piece, and this is of importance because the abrasive particles will be taken into suspension in the water, without danger of direct impingement upon soft tissues or other parts of the mouth.

The block 7 at the end of the handle 5 is provided with passages which interconnect the tubes 8 and 9 with tubes 14 and 15 adapted to cooperate with the flexible supply tubes 16 and 17 for the air-abrasive and water, these flexible tubes 16 and 17 desirably being combined in a common sheath indicated at 18. The flexible tubes 16 and 17 are of course extended to the supply and control equipment which is illustrated in FIGS. 1 and 2.

In considering FIGS. 1 and 2 it is first noted that although various gases may be employed as carrier for the abrasive particles, for instance carbon dioxide, air is suitable and for many purposes is preferred. A line 19 from a source of pressurized air, for instance at from 40 to 80 psi is connected through the filter 20 and the normally closed solenoid shut-off valve 21, with the branch lines 22 and 23. Line 22 is provided with a pressure regulated device 24 which delivers the air through connections 25 and 26 to the abrasive mixing device indicated generally at 27. A pressure gauge 28 indicates the pressure following the reduction by the device 24. The connection 25 is provided with a check valve 29 and the connection 26 with a check valve 30.

As best seen in FIG. 2, the device 27 includes an outer casing 31 having a rounded bottom 32, and with a removable closure 33 at the top, the casing 31 serving as a reservoir for abrasive particles as indicated at 34.

Positioned centrally within the casing 31 is a receptacle or chamber 35 connected with the closure member 33 and projecting downwardly into the casing 31 to provide a central chamber with which the air connection 26 connects. Centrally disposed within the container 35 is a tube 36 which extends through the closure member 33 and is provided with openings with one of which the air connection 25 connects. The lower end of the tube 36 fits in an aperture in the bottom of the container 35 and projects downwardly below the bottom of the container 35 where the tube is provided with ports 37 for receiving abrasive. Additional ports 38 in the bottom of the container 35 provide for delivery of air from the container downwardly into the mass of abrasive, thereby effecting introduction of the abrasive particles from the bottom region of the casing 31 into the tube 36. The delivery line for the abrasive-laden air is indicated at 39 and this line is connected with the upper end of the tube 36, preferably in line with the air supply connection 25, the line 39 being extended through a pinch valve 40 from which the connection 16 delivers the air-abrasive stream to the hand piece, as above described in relation to FIGS. 3 and 4.

The connection 25 is provided with an adjustable needle valve 41 for controlling the amount of air flowing directly to the upper end of the tube 36 of the abrasive mixer. This valve provides for adjustment of the quantity of abrasive picked up by the air stream. When the valve 41 is wide open, a minimum of abrasive will be entrained because the air will readily flow through the line 25 and the connection 39 to the hand piece. As the valve 41 is completely closed, the arrangement then provides for maximum pickup of abrasive, because all of the air reaching the delivery line 39 must pass through the chamber 35 and through the ports 38 and 37, thereby entraining a maximum of the abrasive. If desired a valve 41a may also be provided in branch 26.

Turning now to the water supply system, as shown in FIG. 1 an appropriate pressurized water supply line is indicated at 42, this line delivering water through the filter 43 and through a water pressure regulator 44 to a water heater 45. This water heater is adapted to elevate the temperature of the water, for instance to about 100°F, and thereby provide appropriate temperature for use in the mouth. Desirably the water heater 45 has some storage capacity, so that a supply of the warmed water will always be available for use. The warmed water flows through the line 17 to the hand piece as shown in FIGS. 3 and 4, a shut-off valve 46 being provided so that the water flow may be started and stopped at will by the operator.

While reference has been made to the use of a spray of water, it is to be understood that certain other liquids may be used, for instance liquids having medicaments in solution.

Turning now to the control system for starting and stopping the abrasive stream and the water flow, it is first pointed out that the valve 40, which may desirably be of the "pinch" valve type is provided with a pneumatic actuating device of known type indicated at 47, this device 47 being supplied with actuating air from the branch 23a of the connection 23 above mentioned. The device 47 is under the control of a solenoid operated by the circuit diagrammatically indicated at 48, which circuit is associated with a contact 49 of a switch device mentioned just below.

The water shut-off valve 46 is solenoid operated and the control circuit for that valve is diagrammatically indicated at 50, being associated with the contact 51 of the main control switch. This main control switch desirably comprises a switch arm 52 connected with a current source 53, the switch arm having a contactor adapted to engage either the contact 51 or both of the contacts 51 and 49. Switches of this type are well known and for dental purposes are commonly arranged for foot actuation.

With the arrangement just described, the operator in using the equipment will operate the switch arm 52 and this will initially engage the contact 51, thereby opening the water supply valve 46. By further movement of the arm 52 the contact 49 is engaged, and by opening the valve 40 in order to deliver the air-abrasive stream to the hand piece. It is advantageous that the switch arm 52 may be operated to substantially concurrently initiate flow of both the water and the air-abrasive stream, but it is preferred to employ an arrangement such as shown, so that water alone may be delivered and also so that whenever abrasive is delivered there is assurance that water will also be delivered.

The upper portion of the casing 31 of the abrasive mixer (see FIGS. 1 and 2) is provided with an exhaust port 54 which is connected to atmosphere by the line 55 through a bleed valve 56 and through an abrasive powder trap 57. This valve 56 is normally open and may be of the pinch valve type such as described above with reference to valve 40, the valve 56 being supplied with actuating air pressure through the branch 23b of the line 23, and being under the control of a circuit indicated at 58 which is connected with the contact 59 of a master on-off switch 60. This switch 60 is associated with a power source diagrammatically indicated at 61 and serves not only to operate the valve 56 but further to operate the valve 21 by virtue of the connection 62.

When the equipment is to be used, the switch 60 is closed, thereby opening the normally closed solenoid valve 21 and thereby also closing the normally open valve 56. The flow of the air-abrasive and of the water is then manually controlled by the foot switch 52 in the manner described above. When the equipment is no longer needed for operation, the master shut-off switch 60 may then be opened and the normally closed solenoid valve shuts off the air supply, and in addition the valve 56 opens and provides for bleed-off of the pressure in the system including the abrasive mixing device, discharge of abrasive particles being prevented by the powder trap 57. This automatic bleed-off of pressure is important particularly for the purpose of providing for refilling the abrasive casing 31. If the pressure has been exhausted from the system, the removable closure 33 may be separated in order to permit introduction of a new charge of abrasive.

A valve 63 may be provided in order to adjust the pressure of the air supplied through the connection 23 to the pinch valves 40 and 56.

For prophylaxis purposes it is preferred to employ abrasive particles of very small particle size and of uniformity of particle size, for instance particles of the order of 20–70 microns. It is preferred according to the invention to provide such particles formed of pure Iceland spar. As an alternative, fine microheads of glass may be used, either one of these abrasives being capable of removing stain from the teeth without, however, any appreciable etching effect on the tooth enamel, and thus without any of the possibly detrimental effects which could flow from certain other abrasives, such as free silicates or dolomite.

In addition to various of the advantages mentioned above, the equipment of the present invention is also advantageous in that it eliminates the necessity for drying the teeth prior to cleaning. Bulky suction or vacuum equipment is not needed and since the abrasive is readily removed by means of the customary saliva ejector, separate disposal of the abrasive is not required.

I claim:

1. A handpiece for delivering a stream of air carrying abrasive particles, comprising a nozzle having an abrasive discharge passage for the abrasive laden air stream, the nozzle further having a series of water discharge passages in an array surrounding the abrasive passage, and a water feed passage for supplying water to the passages of said array, the abrasive passage and the water discharge passages being directed in the same general direction to provide for discharge of a water curtain surrounding the discharging abrasive laden air stream, the water discharge passages having their axes inclined to provide converging water streams.

2. A method for cleaning teeth comprising concurrently directing separate streams of a liquid and of an abrasive laden gas against the tooth to be cleaned, the liquid stream being directed in a predetermined converging angular relationship to the gas stream and to an area of the tooth immediately adjacent to the area of impingement of the gas stream.

3. A method for cleaning teeth comprising concurrently directing separate streams of a liquid and of an abrasive laden gas against the tooth to be cleaned, the liquid being delivered in a plurality of streams arranged in an array surrounding the gas stream and the liquid streams being directed in predetermined converging angular relationship to the gas stream and to an annular area of the tooth surrounding and immediately adjacent to the area of impingement of the gas stream.

4. A dental handpiece for use in the cleaning of teeth, the handpiece comprising an elongated hand grip having two separate fluid passages extended longitudinally therethrough providing respectively for supply of abrasive laden gas and of a liquid, the hand grip further having a head at one end thereof with two fluid discharge orifices and with two passages respectively and separately connecting said longitudinal passages with the fluid discharge orifices, the orifices being positioned and oriented to discharge streams of the abrasive laden gas and liquid in the same general direction transversely of the hand grip, with the streams of abrasive laden gas and liquid converging toward each other.

5. A dental handpiece for use in the cleaning of teeth, the handpiece comprising an elongated hand grip having two separate fluid passages extended longitudinally therethrough providing respectively for supply of abrasive laden gas and a liquid, the hand grip further having a head at one end thereof with a fluid discharge orifice for the abrasive laden gas stream, the head having a liquid chamber with an array of discharge orifices surrounding the orifice for the gas stream, two passages in the head respectively and separately connecting said longitudinal passages with the orifice for the gas stream and said chamber, the gas and liquid orifices being positioned and oriented to discharge streams of the abrasive laden gas and liquid in the same general direction transversely of the hand grip with the streams of liquid converging toward the gas stream.

* * * * *